United States Patent
Brown

(10) Patent No.: US 7,806,930 B2
(45) Date of Patent: Oct. 5, 2010

(54) DEVICE FOR ATTACHMENT TO A CAPSULE IN AN EYE

(76) Inventor: David C. Brown, 1195 Caloosa Dr., Fort Myers, FL (US) 33901

( * ) Notice: Subject to any disclaimer, the term of this patent is extended or adjusted under 35 U.S.C. 154(b) by 1688 days.

(21) Appl. No.: 10/971,881

(22) Filed: Oct. 22, 2004

(65) Prior Publication Data

US 2006/0047340 A1    Mar. 2, 2006

Related U.S. Application Data

(63) Continuation-in-part of application No. 10/927,743, filed on Aug. 27, 2004.

(51) Int. Cl.
*A61F 2/16* (2006.01)
(52) U.S. Cl. .................. 623/6.4; 623/6.41; 623/5.12
(58) Field of Classification Search ............ 623/5.13, 623/5.12, 5.14, 5.15, 6.4, 6.41, 6.47, 6.51, 623/6.52, 6.53, 6.54
See application file for complete search history.

(56) References Cited

U.S. PATENT DOCUMENTS

| | | | | |
|---|---|---|---|---|
| 3,996,626 A * | 12/1976 | Richards et al. | ............ | 623/6.46 |
| 4,118,808 A * | 10/1978 | Poler | ................ | 623/6.41 |
| 4,215,440 A | 8/1980 | Worst | ................ | 623/6.43 |
| 4,446,582 A * | 5/1984 | Hanna | ................ | 623/6.51 |
| 4,932,971 A | 6/1990 | Kelman | | |
| 4,946,469 A | 8/1990 | Sarfarazi | | |
| 5,074,876 A | 12/1991 | Kelman | | |
| 5,192,319 A | 3/1993 | Worst | ................ | 623/6.43 |
| 6,068,643 A | 5/2000 | Milverton | | |
| 6,152,959 A * | 11/2000 | Portney | ................ | 623/6.51 |
| 6,261,321 B1 | 7/2001 | Kellan | | |
| 6,280,471 B1 * | 8/2001 | Peyman et al. | ............ | 623/6.17 |
| 6,387,126 B1 | 5/2002 | Cumming | | |
| 6,423,094 B1 | 7/2002 | Sarfarazi | | |
| 6,425,917 B1 * | 7/2002 | Blake | ................ | 623/6.42 |
| 6,488,708 B2 | 12/2002 | Sarfarazi | | |
| 6,554,860 B2 * | 4/2003 | Hoffmann et al. | ......... | 623/6.43 |
| 6,620,098 B1 | 9/2003 | Milverton | ................ | 600/236 |

(Continued)

FOREIGN PATENT DOCUMENTS

WO    WO 03/022191 A1    3/2003

(Continued)

OTHER PUBLICATIONS

"Clearly Exquisite," www.ophthalmologytimes.com, Oct. 1, 2004.

(Continued)

*Primary Examiner*—Paul Prebilic
(74) *Attorney, Agent, or Firm*—John J. Love; Claude E. Cooke; Burleson Cooke, L.L.P.

(57) ABSTRACT

Devices, systems, and methods useful in treating an eye are provided herein. Certain embodiments of the devices, systems, and methods may be particularly suitable in maintaining separation of an anterior capsule and a posterior capsule of an evacuated lens capsule of an eye. Certain embodiments of the devices, systems, and methods may be particularly suitable for reducing scarring in the visual field of an eye having a capsulorhexis, among other things.

3 Claims, 10 Drawing Sheets

U.S. PATENT DOCUMENTS

| | | |
|---|---|---|
| 6,638,306 B2 | 10/2003 | Cumming |
| 6,645,246 B1 | 11/2003 | Weinschenk, III et al. |
| 6,723,124 B2 | 4/2004 | Brady |
| 6,761,737 B2 | 7/2004 | Zadno-Azizi et al. |
| 6,770,093 B2 | 8/2004 | Worst et al. .............. 623/6.12 |
| 2002/0072796 A1* | 6/2002 | Hoffmann et al. .......... 623/6.43 |
| 2002/0091442 A1 | 7/2002 | Snyder |
| 2002/0111678 A1 | 8/2002 | Zadno-Azizi et al. |
| 2002/0116057 A1 | 8/2002 | Ting et al. |
| 2002/0116060 A1 | 8/2002 | Nguyen et al. |
| 2002/0173846 A1 | 11/2002 | Blake et al. |
| 2003/0074060 A1 | 4/2003 | Zadno-Azizi et al. |
| 2003/0074061 A1 | 4/2003 | Pham et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2004/0006387 A1 | 1/2004 | Kelman |
| 2004/0010284 A1 | 1/2004 | Maloof et al. ............... 606/213 |
| 2004/0064182 A1 | 4/2004 | Kelman |
| 2004/0111152 A1 | 6/2004 | Kelman |
| 2005/0015143 A1* | 1/2005 | Willis et al. ................ 623/6.36 |
| 2006/0047339 A1* | 3/2006 | Brown ....................... 623/6.13 |

FOREIGN PATENT DOCUMENTS

| | | |
|---|---|---|
| WO | WO 2004/017877 A1 | 3/2004 |

OTHER PUBLICATIONS

Saini, et al., Anterior and posterior capsulorhexis in pediatric cataract surgery with or without trypan blue dye, Journal of Cataract Refractive Surgery, vol. 29, Sep. 2003.

Presentation entitled, "Upcoming IOL Technology: Multifocal, Accommodative, and Small-Incision," by Richard L. Lindstrom, M.D., presented at Cataract Innovators Symposium (Mar. 26-28, 2004), *reprinted in* Sep. 2004 Supplement to Cataract & Refractive Surgery Today, pp. 15-18, Publication Dated Sep. 2004.

Webpage describing ARTISAN® Myopia products, available at http://www.ophtec.com/eng/prodln/refr/myop/myop.htm, Oct. 8, 2004.

* cited by examiner

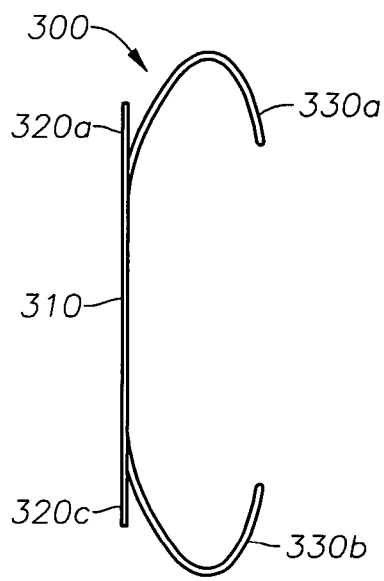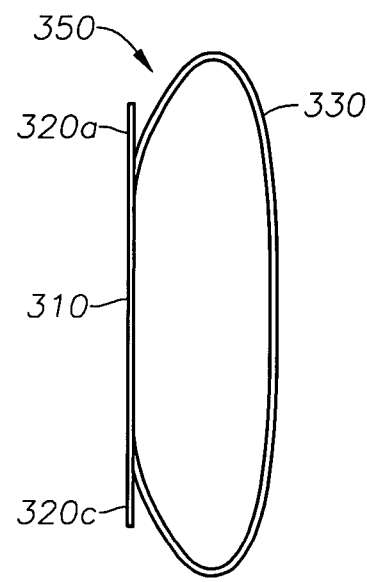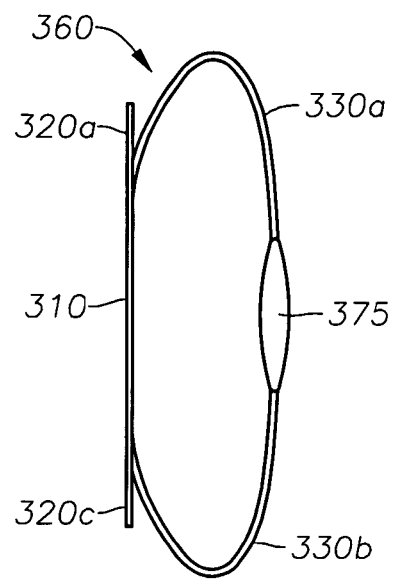
Fig. 3A    Fig. 3B    Fig. 3C
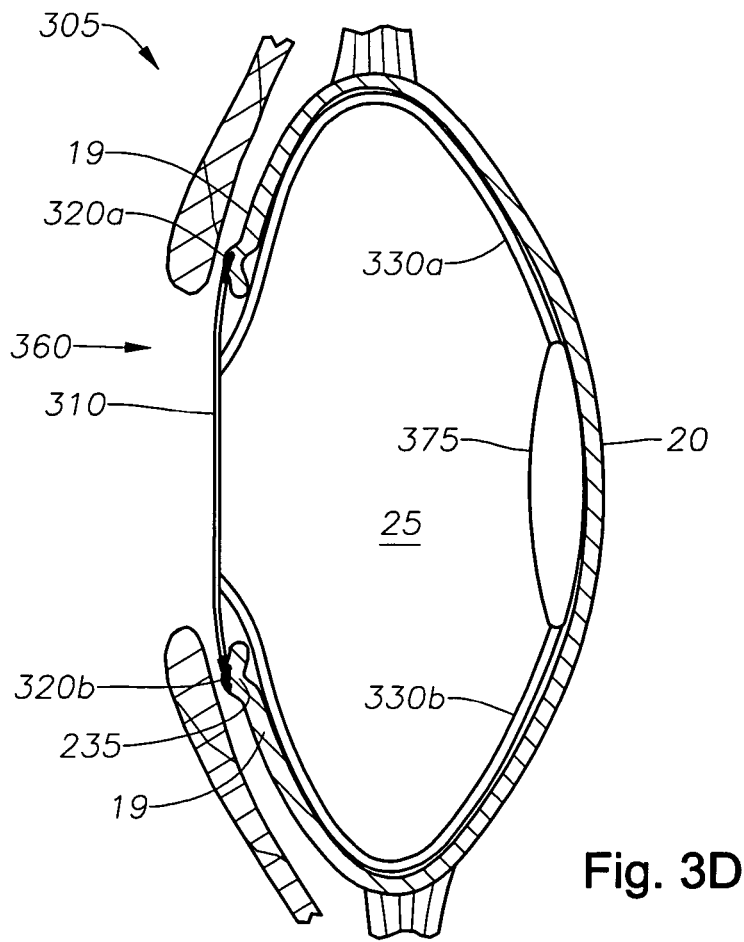
Fig. 3D

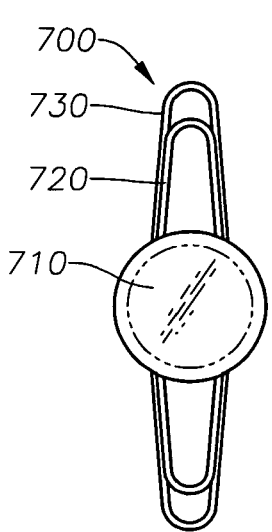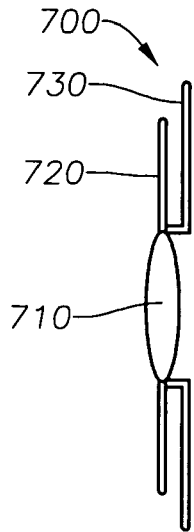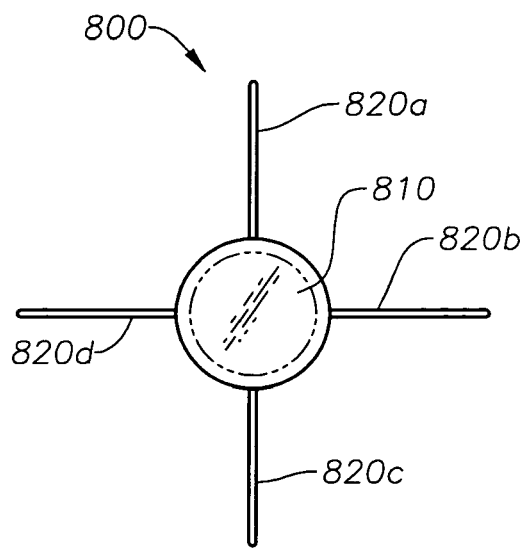
Fig. 7A    Fig. 7B    Fig. 8A
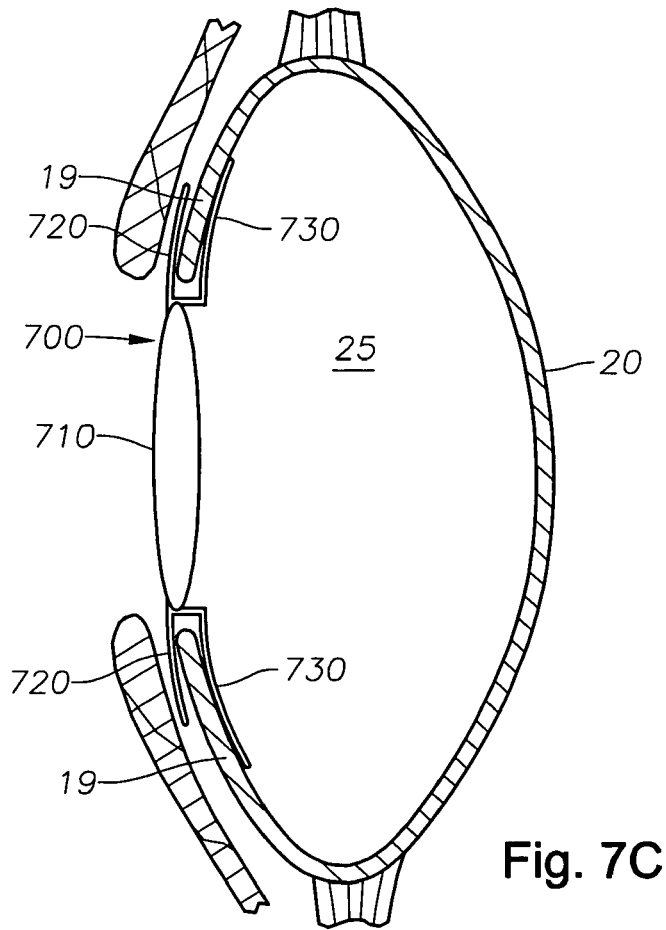
Fig. 7C

DEVICE FOR ATTACHMENT TO A CAPSULE IN AN EYE

CROSS-REFERENCE TO RELATED APPLICATION

This Application is a continuation-in-part of U.S. application Ser. No. 10/927,743, entitled "Intracapsular Pseudophakic Device," filed on Aug. 27, 2004.

BACKGROUND

The present invention pertains to devices, systems, and methods useful in treating an eye. Certain embodiments of the devices, systems, and methods disclosed herein may be particularly suitable in maintaining separation of an anterior capsule and a posterior capsule of an evacuated lens capsule of an eye. Certain embodiments of the devices, systems, and methods disclosed herein may be particularly suitable for reducing scarring in the visual field of an eye having a capsulorhexis.

The human eye has a transparent crystalline lens structure, which is located immediately behind the iris. This crystalline lens is formed from epithelial cells, and the cytoplasm of these cells makes up the transparent substance of the lens. The crystalline lens may be described as having four layers, which layers (identified from the surface of the crystalline lens to the center) are the capsule, subcapsular epithelium, cortex, and nucleus. The lens capsule is a clear, membrane-like structure that is quite elastic, a quality that keeps it under constant tension. As a result, the lens naturally tends towards a rounder or more globular configuration, a shape it must assume for the eye to focus at a near distance. The lens is held in place by slender, strong suspensory ligaments (also known as zonules), which attach at one end to the lens capsule and at the other end to the ciliary processes of the circular ciliary body around the inside of the eye.

The human eye naturally has the ability to focus on both near and far objects by adjusting the shape of the crystalline lens. This adjustment is referred to as "accommodation," and is associated with a concurrent constriction of the pupil. Accommodation occurs with the relaxation and contraction of the ciliary muscle in the ciliary body, which increases or decreases tension on the suspensory ligaments, which in turn acts on the lens capsule around its equator to cause the entire lens to flatten (become less convex) or round (become more convex). When ciliary muscles relax, the lens becomes less convex, and light from more distant objects is focused on the retina. When ciliary muscles contract, the lens becomes more convex and light from closer objects is focused on the retina.

The maximum amount that the crystalline lens can change shape is called the "amplitude of accommodation." The amplitude of accommodation is very high when young, but decreases with age. This normal condition is known as "presbyopia," and may be due both to a lessening of flexibility of the crystalline lens and to a generalized weakening of the ciliary muscle that causes the lens to accommodate.

Furthermore, the crystalline lens often develops a cataract, which is an opaque region or clouding of the lens. This condition leads to widespread application of techniques to remove the crystalline lens. One common procedure, called "extracapsular" cataract extraction, is frequently used to treat a cataract. In this procedure, an opening is made in the front of the lens capsule. Through this opening, the lens nucleus is removed, either as a whole or by dissolving it into tiny pieces and vacuuming out the pieces, a procedure called "phacoemulsification." Next, the lens cortex also is sucked out, leaving the lens capsule in place, at which point a conventional intra-ocular lens (IOL) often is inserted into the lens capsule. When a conventional (monofocal) IOL is implanted, the accommodating ability, if any, is very limited. Accordingly, the wearer or user of the conventional IOL may use corrective spectacles as a useful aid in vision. Multi-focal IOL's without accommodating movement have been used to provide near and far vision correction.

A variety of attempts have been made to provide IOL's with accommodating movement in the eye. One such device is the CRYSTALENS, which was approved for use in the United States in November, 2003. (Another accommodating lens has been approved for use in Europe.) The CRYSTALENS has a single optic attached to hinged haptics. The optic is vaulted in the posterior position against the posterior capsule. Operation of the ciliary muscle increases the pressure in the vitreous humor, moving the optic in an anterior direction, thereby increasing the power of the optic. Relaxation of the ciliary muscle allows the lens to move backward. The forward and backward motion simulates natural lens accommodation. However, the amount of accommodation is limited. The CRYSTALENS normally includes a relatively small optic zone to enhance optic movement, but thereby this increases the chances of nighttime glare and halos.

Likewise, accommodation may be achieved by using optics made of two different materials to enhance the accommodation achievable in the eye in response to normal accommodative stimuli, as disclosed in U.S. Pat. No. 6,645,246.

The creation of an opening in the front of the lens capsule (a "capsulorhexis," such as may be formed during refractive surgery, for example) may give rise to a number of subsequent problems. For example, the capsulorhexis may heal in a manner that may create scar tissue in the field of vision of the eye, which may impair vision through the eye after such healing of the capsulorhexis. As another example, the scar tissue may form during the healing process in a fashion that may displace objects implanted in the lens (e.g., intraocular lens devices, and the like, that may have been implanted during a surgical operation in which the capsulorhexis was created). Such displacement often is undesirable because, inter alia, it may move the implanted object partially, or entirely, outside of the visual axis. Such a situation often is referred to as "decentration," and it may cause, inter alia, blurred vision, double vision, and the like.

Additionally, operations that involve the evacuation of the lens capsule also may be problematic, because, inter alia, the lens capsule may deform after its evacuation, and may fail to attain its original shape even after subsequent placement of a device within the lens capsule. Reduced eye volume may lead to a variety of problems, including, inter alia, retinal detachment. Furthermore, an evacuated lens capsule may impair the accommodation achievable in the eye.

SUMMARY

The present invention pertains to devices, systems, and methods useful in treating an eye. Certain embodiments of the devices, systems, and methods disclosed herein may be particularly suitable in maintaining separation of an anterior capsule and a posterior capsule of an evacuated lens capsule of an eye. Certain embodiments of the devices, systems, and methods disclosed herein may be particularly suitable for reducing scarring in the visual field of an eye having a capsulorhexis.

The features and advantages of the present invention will be readily apparent to those skilled in the art upon a reading of the description of the preferred embodiments that follows.

BRIEF DESCRIPTION OF THE DRAWINGS

The same numerals in different drawings indicate the same parts of an eye and the same parts of a disclosed apparatus.

FIG. 3A shows a cross-sectional view of an embodiment of a device of the present invention.

FIG. 3B shows a cross-sectional view of an embodiment of a device of the present invention.

FIG. 3C shows a cross-sectional view of an embodiment of a device of the present invention.

FIG. 3D shows a cross-sectional view of the anterior portion of a human eye in which the device of FIG. 3C has been placed.

FIG. 7A shows a top plan view of an embodiment of a device of the present invention.

FIG. 7B shows a cross-sectional view of the device of FIG. 7A.

FIG. 7C shows a cross-sectional view of the anterior portion of a human eye in which the device of FIGS. 7A and 7B has been placed.

FIG. 8A shows a top plan view of an embodiment of a device of the present invention.

DESCRIPTION

Figure 1:
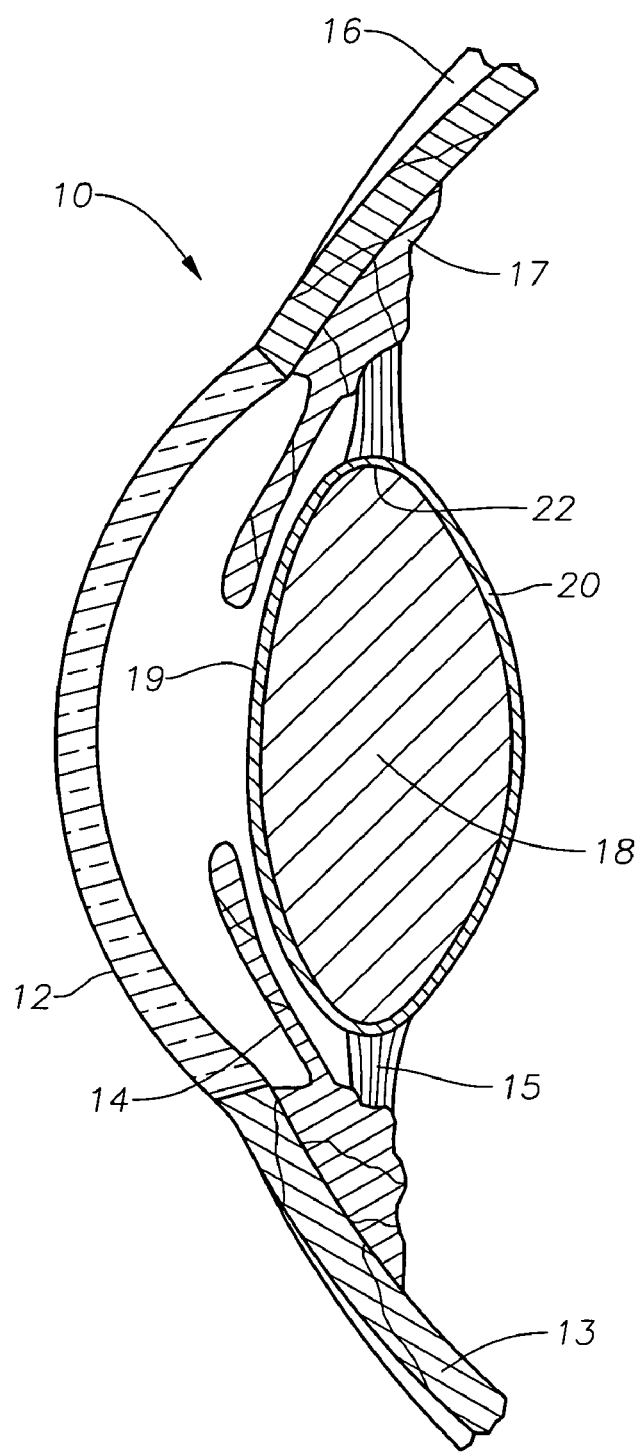
FIG. 1 shows a cross-sectional view of the anterior portion of a human eye.

The present invention pertains to devices, systems, and methods useful in treating an eye. Certain embodiments of the devices, systems, and methods disclosed herein may be particularly suitable in maintaining separation of an anterior capsule and a posterior capsule of an evacuated lens capsule of an eye. Certain embodiments of the devices, systems, and methods disclosed herein may be particularly suitable for reducing scarring in the visual field of an eye having a capsulorhexis.

When placed in the lens of an eye, the devices and systems of the present invention may perform a variety of functions. For example, certain embodiments of the devices, systems and methods of the present invention may be useful in restoring and/or maintaining the clarity of sight through a lens capsule in which an opening has been formed, by, inter alia, preventing the healing of a capsulorhexis from creating scar tissue in the visual axis of the lens capsule. Such devices, systems and methods may be particularly useful, inter alia, in pediatric ophthalmic surgery, where closure of lens capsule openings by tissue growth occurs relatively rapidly. Such devices, systems and methods also may be particularly useful in treating conditions such as, e.g., pseudo-exfoliation syndrome, and the like.

Certain embodiments of the devices, systems and methods of the present invention also may enhance proper positioning of, e.g., a capsular implant that has been placed in a lens capsule through a capsulorhexis, so as to prevent undesirable displacement of such implant from occurring as the capsulorhexis heals. Accordingly, in certain embodiments of the present invention, a device of the present invention may be placed in a capsulorhexis to maintain the proper position of a posteriorly placed device (which posteriorly placed device also may be a device of the present invention, or may be another device that presently is known in the art, or that someday may become known in the art). In certain embodiments of the present invention, such device of the present invention may comprise haptics that further facilitate maintenance of the proper position of the posteriorly placed device.

Certain embodiments of the devices, systems, and methods of the present invention may restore and/or maintain the conformation and/or volume of a lens capsule that has been wholly or partly evacuated (e.g., a lens capsule from which crystalline lens 18 (shown in FIG. 1) has been wholly or at least partially evacuated). Such restoration and/or maintenance of the conformation and/or volume of the lens capsule may, inter alia, enhance the overall health of the eye, and may enable and/or improve accommodation.

Accordingly, certain embodiments of the devices and systems of the present invention may be suitable for use as, inter alia, optical devices or tectonic devices. For example, certain embodiments of the devices and systems of the present invention may be used as an artificial anterior capsule to repair the lens capsule of an eye. Certain embodiments of the devices and systems of the present invention also may be used to provide optical correction to an eye. Certain embodiments of the devices and systems of the present invention, when used alone or in combination with other ocular devices, may permit and/or enhance accommodation. Certain embodiments of the systems and devices of the present invention may be used singly, or may be used in combination with other embodiments of the systems and devices of the present invention, or with devices known in the art, or with devices that may become known in the art.

Referring now to FIG. 1, illustrated therein is a saggittal view of the anterior portion of an eye 10, which may be a human eye, in certain embodiments of the present invention. Eye 10 includes cornea 12, sclera 13, iris 14, zonules 15, conjunctiva 16, ciliary body 17, crystalline lens 18, anterior capsule 19, posterior capsule 20 and capsule equator or fornix 22. The development of presbyopia and cataracts in the human eye are associated with changes in the natural crystalline lens 18. Surgical procedures to remove cataracts from the crystalline lens 18 or to implant IOLs, either accommodating or fixed, generally involve making an incision through cornea 12 or sclera 13 and forming an opening in anterior capsule 19 and/or posterior capsule 20 (e.g., a "capsulorhexis", such as capsulorhexis 225, illustrated in FIG. 2H). A capsulorhexis also may be referred to by the terms "capsulotomy," "anterior capsule opening," and "lens capsule opening," in various portions of this disclosure. Generally, surgeons endeavor to minimize the size of the capsulorhexis, inter alia, to limit trauma to eye 10 and allow faster healing. Commonly, a capsulorhexis may have a diameter in the range of from about 2.5 to about 3 millimeters; however, a trend recently has emerged that involves smaller incisions, such as about 1.5 millimeter in diameter.

Figure 2A:
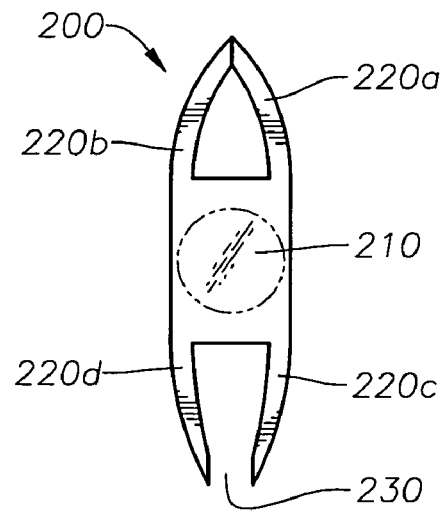
FIG. 2A shows a top plan view of an embodiment of a device of the present invention.

Referring now to FIG. 2A, a top plan view illustrates therein an embodiment of a device of the present invention. Device 200 comprises central membrane 210 and pincer arms 220a-220d. In certain embodiments of the present invention, central membrane 210 may comprise a deformable membrane. In general, deformable membranes suitable for use in the present invention should be formed from a deformable material suitable for biomedical use, such as those deformable materials disclosed in U.S. patent application 2002/0175846, for example, the relevant disclosure of which is incorporated herein by reference. Suitable deformable membranes are known in the art and may be selected based on factors such as, inter alia, material modulus, and other physical properties.

In certain embodiments of the present invention, pincer arms 220a-220d may be formed from any flexible material. In certain embodiments of the present invention, pincer arms 220a-220d may be formed, at least in part, from an elastomeric biomedically approved material, such as, e.g., silane materials, acrylic polymeric materials, combinations of such materials, and the like. Pincer arms 220a-220d attach device 200 to a portion of a capsule (e.g., anterior capsule 19 and posterior capsule 20 of FIG. 1). The articulation of the pincer arms is illustrated in FIG. 2A. Pincer arms 220a and 220b are illustrated in a "closed" configuration, such as could occur before the placement of a portion of a capsule (which may be a "fold" of a capsule) between pincer arms 220a and 220b. Pincer arms 220c and 220d are shown in an "open" configuration, with gap 230 present between pincer arms 220c and 220d. Pincer arms 220a-220d may attach device 200 to a portion of a capsule upon, for example, the insertion of a portion of anterior capsule 19 or posterior capsule 20 between two adjacent opposing pincer arms (e.g., between pincer arm 220d and pincer arm 220c, or between pincer arm 220a and pincer arm 220b). In this way pincer arms 220a-220d may grasp a portion of anterior capsule 19 or posterior capsule 20, thereby fixing device 200 to such portion of the anterior capsule 19 and/or posterior capsule 20. An illustration of the placement of a portion of a capsule between two adjacent opposing pincer arms may be seen in FIG. 2G, which depicts pincer arms 220a and 220b attached to fold 235 of a capsule.

Figure 2B:
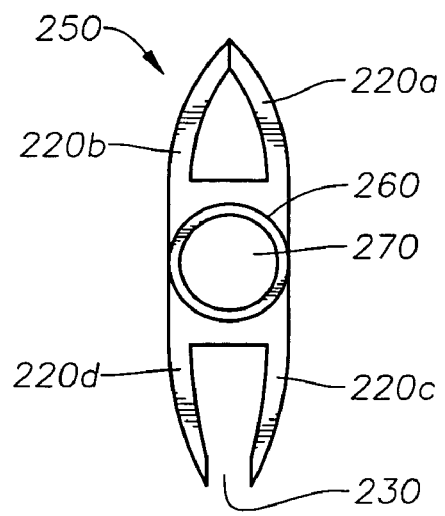
FIG. 2B shows a top plan view of an embodiment of a device of the present invention.

Referring now to FIG. 2B, a top plan view illustrates therein another embodiment of a device of the present invention. Device 250 comprises ring 260 having opening 270 centrally disposed therein, and pincer arms 220a-220d. Generally, ring 260 may be formed using any biocompatible material. For example, ring 260 may be formed from elastomeric materials such as, e.g., silane materials or other such materials that may be suitable for placement in an eye.

Figure 2C:
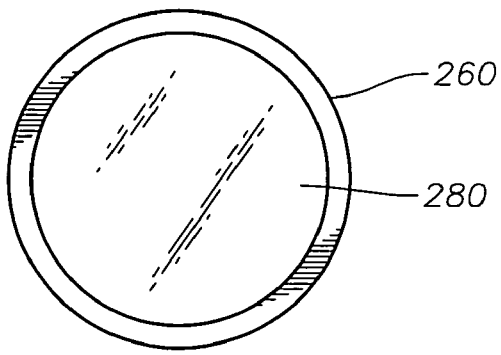
FIG. 2C shows a top plan view of a ring used in an embodiment of a device of the present invention.

In certain embodiments of the present invention, opening 270 may be replaced by membrane 280, which may be centrally disposed within on ring 260, as shown in FIG. 2C. Membrane 280 may be attached to ring 260 in a variety of ways. For example, membrane 280 may be integrally formed with ring 260, or may be inserted in ring 260 separately and latched in place, such as in a groove (not shown) around the periphery of ring 260. Membrane 280 may be formed from a deformable material, as has been previously described herein with reference to membrane 210 of device 200.

Figure 2D:
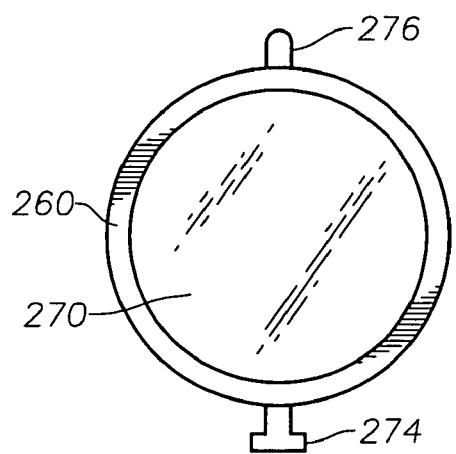
FIG. 2D shows a top plan view of a ring used in an embodiment of a device of the present invention.

In certain embodiments of the present invention, cleats 274 and 276 may be attached to ring 260, as illustrated in FIG. 2D. Suitable cleats are described further in commonly-owned U.S. patent application Ser. No. 10/027,743, the relevant disclosure of which is incorporated herein by reference.

In certain embodiments of the present invention, an optic (not shown in FIG. 2D) may be incorporated within a device of the present invention in a variety of ways. For example, such optic integrally formed with membrane 280, or may be attached to ring 260, e.g., by cleats 274 and 276. Suitable optics may comprise, inter alia, rigid lenses, or lenses that are adaptable to folding or rolling for insertion in the eye through an incision. Such adaptable lenses are widely used in the art. In certain embodiments, the optic may be a light-adjustable lens, such as is available from Calhoun Vision, Inc., Pasadena, Calif., disclosed in U.S. patent application Publication No. 2003/0174375, published Sep. 18, 2003, the relevant disclosure of which is incorporated herein by reference. In certain embodiments of the present invention, the optional optics may be bi-convex optics. In certain embodiments of the present invention, the optional optics also may be planar, concave, or suitable combinations thereof.

Figure 2E:
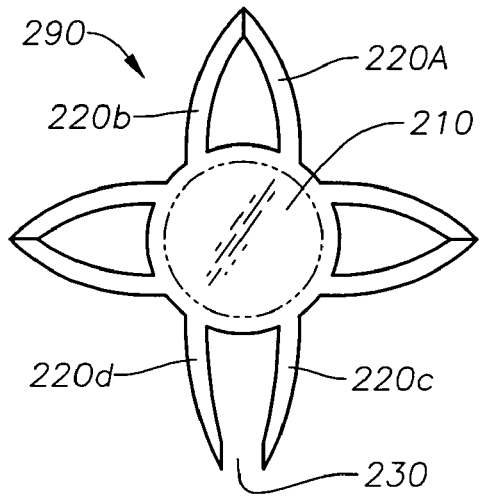
FIG. 2E shows a top plan view of an embodiment of a device of the present invention.

Referring now to FIG. 2E, a top plan view illustrates therein another embodiment of a device of the present invention. Device 290 of the present invention is shown comprising pincer arms 220A, 220b, 220c and 220d, along with membrane 210. Gap 230 is shown between pincer arms 220c and 220d. In certain embodiments of the present invention, device 290 may not comprise membrane 210, but rather may comprise ring 260 having opening 270 (ring 270 and opening 270 not shown in FIG. 2E).

Figure 2F:
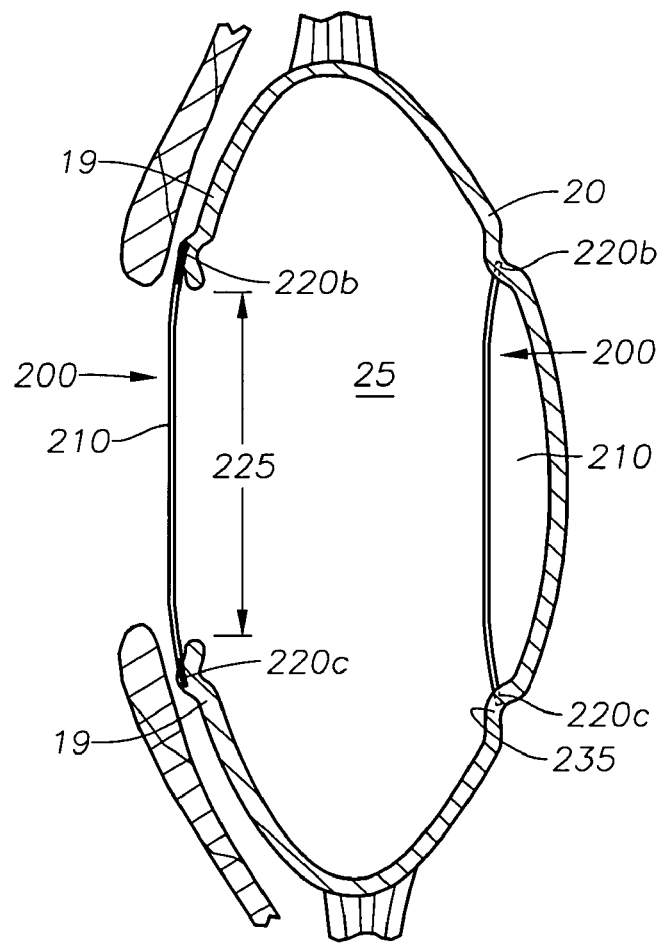
FIG. 2F shows a cross-sectional view of the anterior portion of a human eye in which the device of FIG. 2A has been placed.
Figure 2G:
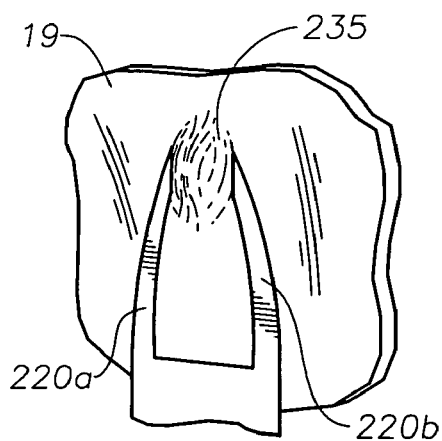
FIG. 2G shows an expanded view of a pincer of an embodiment of a device of the present invention attached to a portion of an anterior capsule of a human eye.

Referring now to FIG. 2F, a cross-sectional view is illustrated therein that depicts device 200 of the present invention disposed on an external portion of anterior capsule 19, and another device 200 of the present invention is illustrated on an inside portion of posterior capsule 20. For ease of illustration, the illustrated eye is aphakic; e.g., crystalline lens 18 of FIG. 1 has been removed. Accordingly, the illustrated eye has cavity 25. It will be apparent to one of ordinary skill in the art, however, that certain embodiments of the devices of the present invention may, and often will, be used in an eye having crystalline lens 18 in place (e.g., a phakic eye), or having crystalline lens 18 partially in place. Capsulorhexis 225 has been formed in anterior capsule 19. Pincer arms 220a-220d pinch (e.g., attach to) "folds" of anterior capsule 19 adjacent the periphery of capsulorhexis 225, thereby positioning device 200. Device 200 is also shown attached to posterior capsule 20 in the same way. FIG. 2F illustrates pincer arms 220c and 220d "pinching" fold 235 of posterior capsule 20. For simplicity, only one fold 235 is specifically identified by number in FIG. 2F. Like device 200, devices 250 and 290 may be placed on the interior surface of posterior capsule 20, and also may be placed on the interior or exterior surface of anterior capsule 19. Forceps, an injector, or other device well known to surgeons may be used for placement.

Placement of device 200, 250, or 290 in the posterior capsule may afford such devices greater mobility along the visual axis in response to ciliary muscle action, thereby facilitating accommodation. By way of explanation, and not of limitation, greater mobility along the visual axis may result from the way that such devices attach to posterior capsule 20. In certain embodiments of the present invention, devices 200, 250, and 290 may be placed in posterior capsule 20 without supporting haptics.

In certain optional embodiments of the present invention, after placement of a device using pincer arms, (e.g., devices 200, 250, and 290 of the present invention), the attachment of such devices to the capsule further may be enhanced. For example, after placement of device 200 in anterior capsule 19 (shown in FIG. 2h), device 200 may be glued to anterior capsule 19, e.g., using a tissue adhesive. In some embodiments, a material, e.g., a fluid or a gel, may be introduced into anterior capsule 19 and retained therein, which may further enhance the attachment of the device, e.g., device 200, to anterior capsule 19. In this application, the attachment is made such that the device may seal the material within the capsule. Capsules comprising material and a device sealed to the capsule may be useful when the conformation and/or volume of the capsule should be maintained. Likewise, this may be useful in applications directed at facilitating accommodation.

Referring now to FIG. 3A, illustrated therein is a side view of another embodiment of a device of the present invention. Device 300 comprises membrane 310, pincer arms 320a and 320c, and haptics 330a and 330b. Device 300 has four pincer arms, but only pincer arm 320a and 320c are visible in the side view of FIG. 3A. Membrane 310 and pincer arms 320a and 320c may be formed as has been previously described herein (e.g., as described for device 200). Haptics 330a and 330b may be integrally formed with pincer arms 320a and 320c, and/or with membrane 310, or may be attached by various known mechanical attachment methods.

Haptics 330a and 330b may function in a variety of ways. For example, haptics 330a and 330b may function as a spacer, e.g., to ensure or to enhance centration of device 300 within an eye. As another example, haptics 330a and 330b may serve to support anterior capsule 19, and may ensure or enhance proper positioning of a device (not shown in FIG. 3d) that may be positioned in posterior capsule 20. Haptics 330a and 330b may serve to maintain the configuration and/or volume of capsule 18. Other uses and functions also are possible, including, inter alia, combinations of those described immediately above.

In certain embodiments of the present invention, haptics 330a and 330b may be of any suitable configuration. In one embodiment of the present invention, haptics 330a and 330b are in a spiral configuration and formed from a deformable material suitable for biomedical use, as described in commonly-owned U.S. patent application Ser. No. 10/027,743, the relevant disclosure of which is incorporated herein by reference. Such deformable materials for haptics are well known in the art and may be selected based on factors such as, inter alia, available material modulus and other physical properties. The spiral configuration may be formed from strands of, e.g., polymeric material. Alternatively, strands of, e.g., polymeric material, may be used to form haptics without formation of the spiral configuration. In certain embodiments of the present invention, haptics 330a and 330b may be linearly extended in the absence of a force on the haptic, or haptics 330a and 330b may be formed to a preset position (such as, but not limited to, a position that may conform to the shape of anterior capsule 19 (shown in FIG. 1) in the absence of a bending force on the haptic), before insertion in an eye. In certain embodiments of the present invention, haptics 330a and 330b also may be curved in a plane parallel to the lens plane. In certain embodiments of the present invention, haptics 330a and 330b may be deformable; for example, haptics 330a and 330b may be placed into a position near membrane 310 to facilitate placement of device 300 in an eye (e.g., by folding and/or rolling). The modulus of the material used to form a spiral haptic, and/or the cross-sectional area of the material along the length of the haptic, may be varied in a selected manner so as to provide variable resistance force to bending along the haptic. For example, a lowered cross-section area or lowered elastic modulus material may be placed about one-third the distance from the proximate end of the haptic (e.g., where it is joined to pincer arms 320a and 320c or membrane 310) and about one-third the distance from the distal end of the haptic. The spacing of such more deformable segments along a haptic may be selected to allow the haptic to conform more closely to, e.g., posterior capsule 20 (shown in FIG. 1), capsule fornix 22 (shown in FIG. 1), and/or anterior capsule 19 (shown in FIG. 1). Optimum properties and configurations of haptics 330a and 330b may be selected via, e.g., experiments with haptics having different initial shapes, and placement of varying resistance to bending of haptics in different locations, coupled with observation of configurations of the haptics on device placed within simulated lens capsules, along with the knowledge already possessed by those of ordinary skill in the art, with the benefit of this disclosure.

In certain embodiments of the present invention, device 300 may not comprise membrane 310, but rather may comprise ring 260 having opening 270 (ring 270 and opening 270 not shown in FIG. 3A).

Referring now to FIG. 3B, illustrated therein is a side view of another embodiment of a device of the present invention. Device 350 is illustrated in FIG. 3B comprising membrane 310, pincer arms 320a and 320c, and haptic 330. Device 350 has four pincer arms, but only pincer arm 320a and 320c are visible in FIG. 3B. Membrane 310 and pincer arms 320a and 320c may be formed as has been previously described herein. Haptic 330 may be integrally formed with pincer arms 320a and 320c, membrane 310, or may be attached by various known mechanical attachment methods. Haptic 330 may be formed as has been previously described herein (e.g., as previously described for haptics 330a and 330b above). In device 350, a single haptic 330 is illustrated, having a loop-like configuration. When placed in a capsule, this configuration may, inter alia, circumscribe the entire inner aspect of the posterior capsule 20 (FIG. 1). Haptic 330 generally is configured so as not to interfere with the visual axis when placed in anterior capsule 19 (shown in FIG. 1). In certain embodiments of the present invention, device 350 may not comprise membrane 310, but rather may comprise ring 260 having opening 270 (ring 270 and opening 270 not shown in FIG. 3a).

Referring now to FIG. 3C, device 360 is shown in side view according to one embodiment of the present invention. Device 360 comprises membrane 310, pincer arms 320a and 320c, haptics 330a and 330b, and optic 375. Device 360 has four pincer arms, but only pincer arms 320a and 320c are visible in FIG. 3C. Membrane 310 and pincer arms 320a and 320c may be formed as previously described herein. Haptics 330a and 330b may be integrally formed with pincer arms 320a and 320c, and/or membrane 310, or may be attached by various known mechanical attachment methods. Haptics 330a and 330b may be formed as previously described herein. In device 360, haptics 330a and 330b of device 360 are attached to optic 375. Optic 375 may be any suitable optic, for example, any of the optics described herein. In certain embodiments of the present invention, device 360 may not comprise membrane 310, but rather may comprise ring 260 having opening 270 (ring 270 and opening 270 not shown in FIG. 3a).

Referring now to FIG. 3d, the placement of device 360 in cavity 25 is illustrated in a cross-sectional view. Pincer arms 320a-320d pinch the ends of anterior capsule 19 adjacent the periphery of capsulorhexis 225, thereby positioning device 360. Haptics 330a and 330b provide support for anterior capsule 19 and posterior capsule 20, in a manner that may enhance separation of anterior capsule 19 and posterior capsule 20, and that may enhance the volume of cavity 25 to a desired volume, which in certain embodiments may be a volume that may approach or equal that of a normal capsule volume (e.g., the volume of the capsule prior to its evacuation). In addition, haptics 330a and 330b may be formed so as to maintain optic 375 in contact with posterior capsule 20 as it moves in response to ciliary muscle action, which may produce accommodation.

In certain embodiments of the present invention, a second, "anterior" optic (not shown in FIG. 3C) may be integrally formed with membrane 310 or attached to ring 260 (not shown in FIG. 3C). In these embodiments, device 360 may function as an accommodating IOL. Movement of the second, "anterior" optic (not shown) and posterior optic 375 in an anterior or posterior direction, caused by ciliary muscle 17 (shown in FIG. 1), may provide accommodation.

Figure 4A:
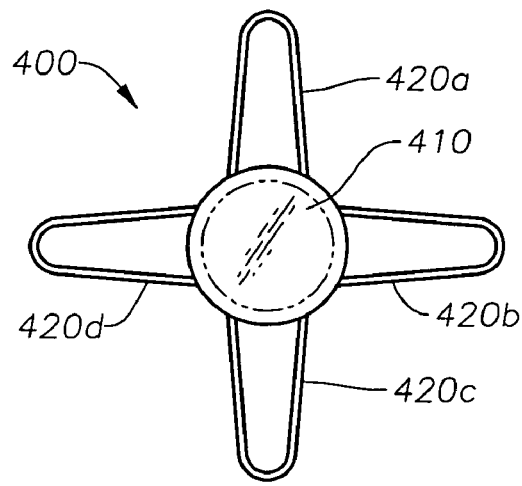
FIG. 4A shows a top plan view of an embodiment of a device of the present invention.

Referring now to FIG. 4A, a top plan view of another embodiment of a device of the present invention is illustrated therein. Device 400 comprises membrane 410 and haptics 420a-420d. Membrane 410 may be formed as has been previously described herein. Haptics 420a-420d are configured around membrane 410. The configuration of haptics 420a-420d may allow device 400 to be more easily folded for insertion into the eye and/or cavity 25 (not shown in FIG. 4a). Each of haptics 420a-420d forms an elongated loop, which may be deformable, and which may be formed of a deformable and biocompatible material. Haptics 420a-420d may be integrally formed with membrane 410 or may be attached by various known mechanical attachment methods. In certain embodiments of the present invention, device 400 may not comprise membrane 410, but rather may comprise ring 260 having opening 270 (ring 270 and opening 270 not shown in FIG. 4A).

Figure 4B:
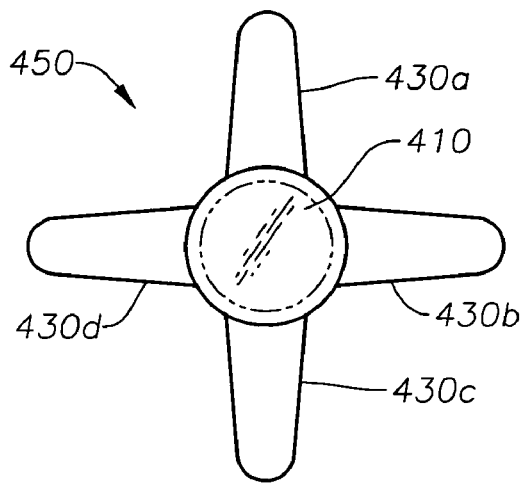
FIG. 4B shows a top plan view of an embodiment of a device of the present invention.

Referring now to FIG. 4B, illustrated therein is a top plan view of another embodiment of a device of the present invention. Device 450 comprises membrane 410 and haptics 430a-430d. Membrane 410 may be formed as has been previously described herein. Haptics 430a-430d are configured around membrane 410. The configuration of haptics 430a-430d may allow device 400 facilitate insertion of device 450 into the eye (not shown in FIG. 4B). As illustrated in FIG. 4B, each of haptics 430a-430d may have a petal-like shape, and may be deformable, and may be formed of a deformable and biocompatible material. Haptics 430a-430d may be integrally formed with membrane 410 or may be attached by various known mechanical attachment methods. In certain embodiments of the present invention, device 450 may not comprise membrane 410, but rather may comprise ring 260 having opening 270 (ring 270 and opening 270 not shown in FIG. 4B).

Figure 4C:
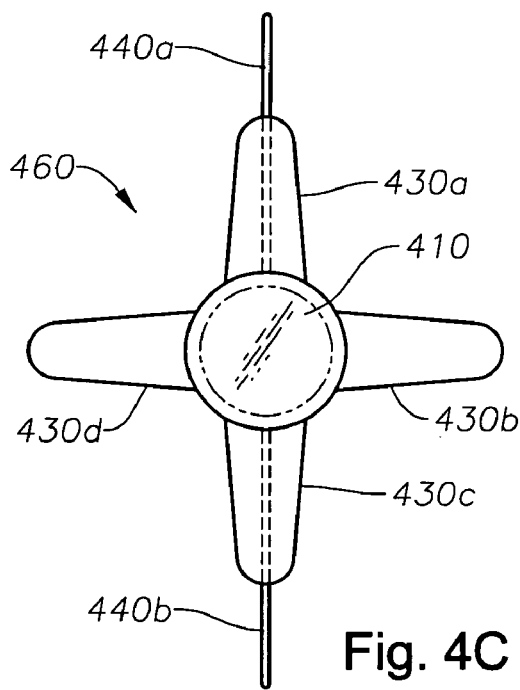
FIG. 4C shows a top plan view of an embodiment of a device of the present invention.
Figure 4D:
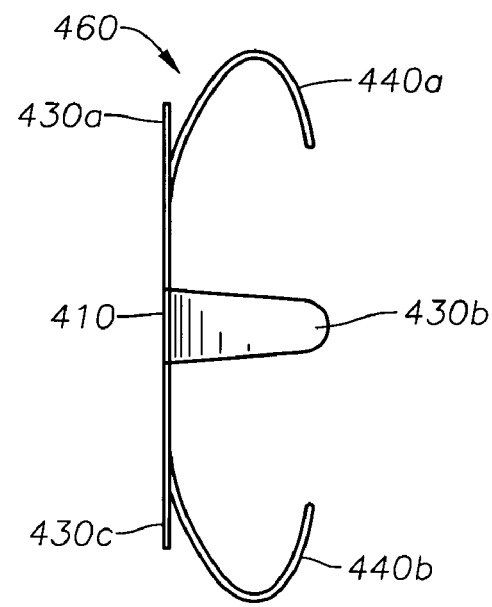
FIG. 4D shows a side view of the device of FIG. 4C.

Referring now to FIG. 4C, illustrated therein is a top plan view of another embodiment of a device of the present invention. Device 460 is illustrated comprising membrane 410, haptics 430a-430d, and haptics 440a and 440b. Haptics 440a and 440b may be integrally formed with membrane 410, integrally formed with haptics 440a and 440b, or may be attached by various known mechanical attachment methods. In certain embodiments of the present invention, haptics 440a and 440b may resemble, e.g., haptics 330a and 330b of device 300, described above. FIG. 4D shows a side view of an embodiment of device 460, in which haptics 440a and 440b are shown integrally formed with, and extending from, membrane 410. In certain embodiments of the present invention, device 460 may not comprise membrane 410, but rather may comprise ring 260 having opening 270 (ring 270 and opening 270 not shown in FIG. 4D).

Figure 4E:
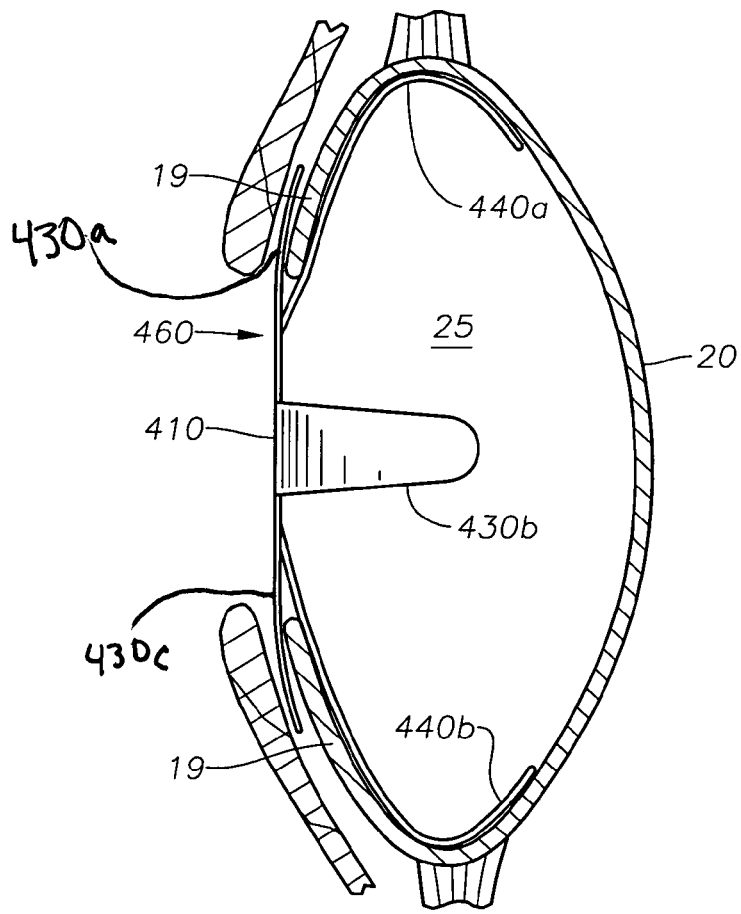
FIG. 4E shows a cross-sectional view of the anterior portion of a human eye in which the device of FIGS. 4C and 4D has been placed.

Referring now to FIG. 4E, the placement of device 460 in cavity 25 is illustrated in a cross-sectional view. Haptics 430a and 430c are illustrated as disposed along an exterior surface of anterior capsule 19, while haptics 440a and 440b are disposed along an interior surface of anterior capsule 19. Haptics 430a-430d in this configuration may, inter alia, enhance the stability of device 460 in anterior capsule 19. Haptics 440a and 440b may support anterior capsule 19 and posterior capsule 20, in a manner that may enhance separation of anterior capsule 19 and posterior capsule 20, and that may enhance the volume of cavity 25 to a desired volume, which in certain embodiments may be a volume that may approach or equal that of a normal capsule volume (e.g., the volume of the capsule prior to its evacuation).

Figure 5A:
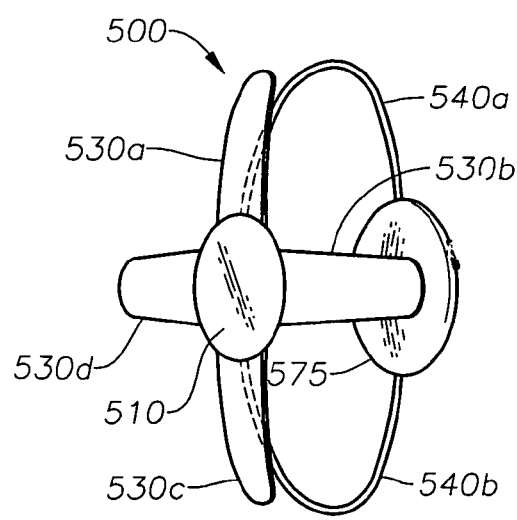
FIG. 5A shows an isometric view of an embodiment of a device of the present invention.

Referring now to FIG. 5A, illustrated therein is a side view of another embodiment of a device of the present invention. Device 500 comprises membrane 510, haptics 530a-530c (530d not shown), haptics 540a and 540b, and optic 575. Optic 575 may be any suitable optic, for example, any of the optics previously described herein. Haptics 540a and 540b may be integrally formed with haptics 530a and 530c, and/or membrane 510, or may be attached by various known mechanical attachment methods. Haptics 530a and 530b may be formed, e.g., as previously described for device 400 and/or 450 above. Haptics 540a and 540b of device 500 are attached to optic 575. In certain embodiments of the present invention, device 500 may not comprise membrane 510, but rather may comprise ring 260 having opening 270 (ring 270 and opening 270 not shown in FIG. 5A).

Figure 5B:
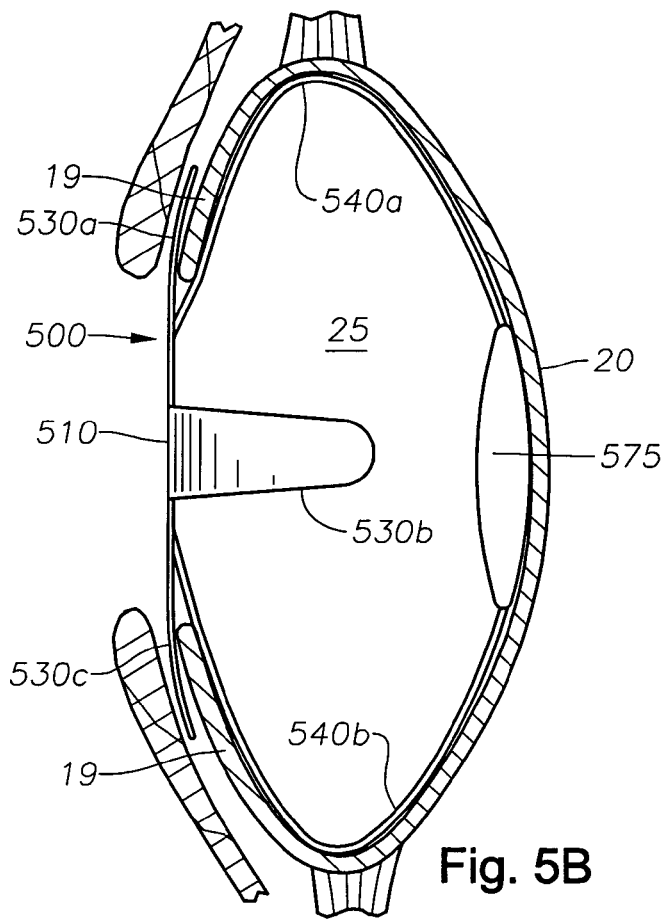
FIG. 5B shows a cross-sectional view of the anterior portion of a human eye in which the device of FIG. 5A has been placed.

Referring now to FIG. 5B, the placement of device 500 in cavity 25 is illustrated in a cross-sectional view. Haptics 530a and 530c are shown disposed along an exterior surface of anterior capsule 19, while haptics 530b and 530d are shown disposed along an interior surface of anterior capsule 19. Haptics 530a-530d in this configuration may, inter alia, enhance the stability of device 500 in anterior capsule 19. Haptics 540a and 540b may support anterior capsule 19 and posterior capsule 20, in a manner that may enhance separation of anterior capsule 19 and posterior capsule 20, and that may enhance the volume of cavity 25 to a desired volume, which in certain embodiments may be a volume that may approach or equal that of a normal capsule volume (e.g., the volume of the capsule prior to its evacuation).

In certain embodiments of the present invention, a second, "anterior" optic (not shown in FIG. 5B) may be integrally formed with membrane 510 or attached to ring 260 (not shown in FIG. 5B). In these embodiments, device 500 may function as an accommodating IOL. Movement of the second, "anterior" optic (not shown) and posterior optic 575 in an anterior or posterior direction, caused by ciliary muscle 17 (shown in FIG. 1), may provide accommodation.

Figure 6E:
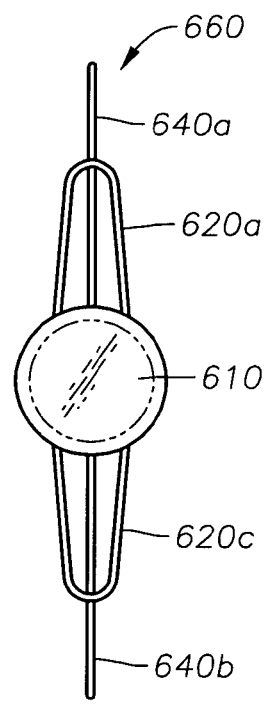
FIG. 6E shows a top plan view of an embodiment of a device of the present invention.
Figures 6A, 6B, 6C, 6D:
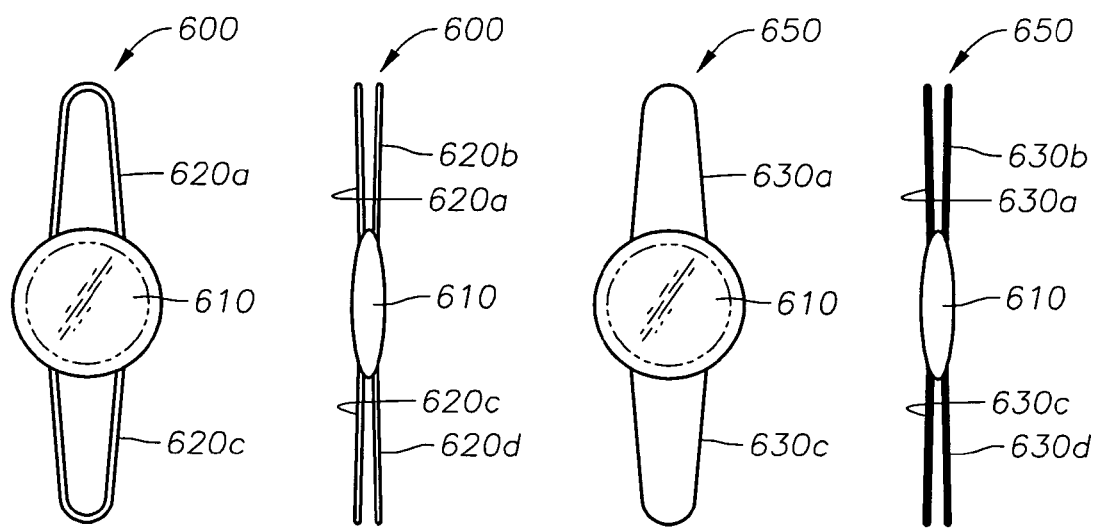
FIG. 6A shows a top plan view of an embodiment of a device of the present invention.
FIG. 6B shows a cross-sectional view of the device of FIG. 6A.
FIG. 6C shows a top plan view of an embodiment of a device of the present invention.
FIG. 6D shows a cross-sectional view of the device of FIG. 6C.

Referring now to FIG. 6A, illustrated therein is a top plan view of another embodiment of a device of the present invention. Device 600 comprises membrane 610 and haptics 620a, 620b, 620c, and 620d (haptics 620b and 620d not shown in FIG. 6A). Membrane 610 may be formed as previously described herein. Haptics 620a and 620c (and haptics 620b and 620c, which are not shown in FIG. 6A) are configured across membrane 610, in opposing fashion from one another (e.g., haptic 620a opposes haptic 620c). FIG. 6B shows a side view of device 600 of the present invention. The configuration of haptics 620a-620d may, inter alia, facilitate folding of device 600, which may facilitate insertion of device 600 into the eye and/or cavity 25 (not shown in FIG. 6A or FIG. 6B). As illustrated in FIG. 6A, each of haptics 620a-620d forms an elongated loop, which may be deformable, and which may be formed of a deformable and biocompatible material. Haptics 620a-620d may be integrally formed with membrane 610, or may be attached by various known mechanical attachment methods. In certain embodiments of the present invention, device 600 may not comprise membrane 610, but rather may comprise ring 260 having opening 270 (ring 270 and opening 270 not shown in FIG. 6A).

Referring now to FIG. 6C, illustrated therein is a top plan view of another embodiment of a device of the present invention. Device 650 comprises membrane 610 and haptics 630a, 630b, 630c and 630d (haptics 630b and 630d not shown in FIG. 6B). Membrane 610 may be formed as previously described herein. Haptics 630a and 630c (and haptics 630b and 630c not shown in FIG. 6C) are configured across membrane 610 in opposing fashion from one another (e.g., haptic 630a opposes haptic 630c). FIG. 6D shows a side view of device 650. The configuration of haptics 630a-630d may, inter alia, facilitate folding of device 600, which may facilitate insertion of device 600 into the eye and/or cavity 25 (not shown in FIG. 6A or FIG. 6B). As illustrated in FIG. 6C, each of haptics 630a-630d may form a petal-type shape, which may be deformable, and which may be formed of a deformable and biocompatible material. Haptics 630a-630d may be integrally formed with membrane 610, or may be attached by various known mechanical attachment methods. In certain embodiments of the present invention, device 650 may not comprise membrane 610, but rather may comprise ring 260 having opening 270 (ring 270 and opening 270 not shown in FIG. 6C or 6D).

Referring now to FIG. 6E, illustrated therein is a top plan view of another embodiment of a device of the present invention. Device 660 comprises membrane 610, haptics 620a and 620c (and haptics 620b and 620c, which are not shown in FIG. 6E), and haptics 640a and 640b. Haptics 640a and 640b are integrally formed with membrane 610. In certain embodiments of the present invention, haptics 640a and 640b may be integrally formed with haptics 620a and 620c, or may be integrally formed with haptics 620b and 620d (not shown in FIG. 6e), or may be attached by various known mechanical attachment methods. Haptics 640a and 640b may resemble haptics 330a and 330b of device 300, described above. In certain embodiments of the present invention, device 660 may not comprise membrane 610, but rather may comprise ring 260 having opening 270 (ring 270 and opening 270 not shown in FIG. 6E).

Figure 6G:
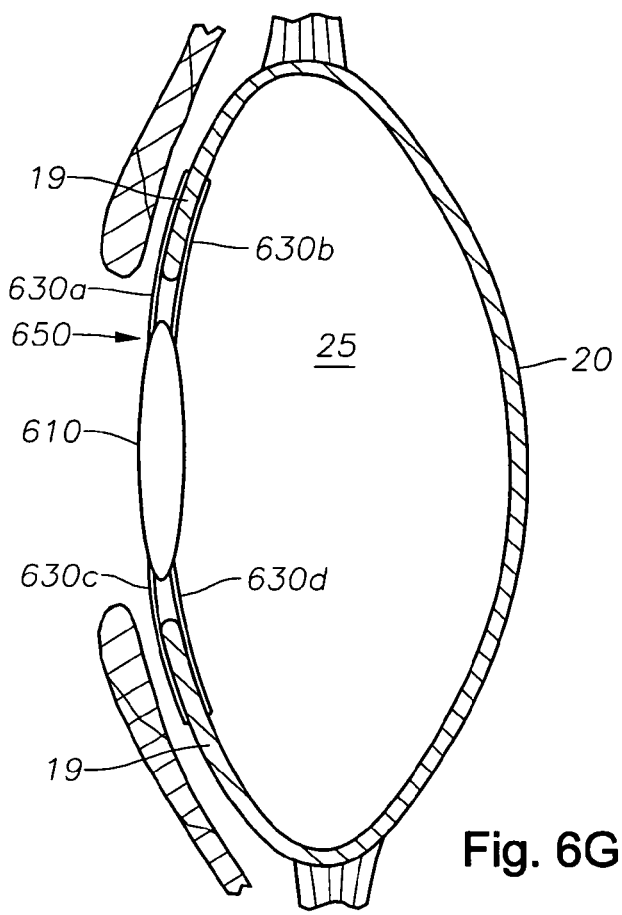
FIG. 6G shows a cross-sectional view of the anterior portion of a human eye in which the device of FIGS. 6C and 6D has been placed.
Figure 6F:
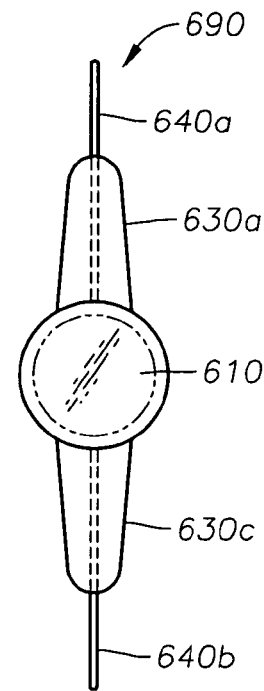
FIG. 6F shows a top plan view of an embodiment of a device of the present invention.

Referring now to FIG. 6F, illustrated therein is a top plan view of another embodiment of a device of the present invention. Device 690 comprises membrane 610, haptics 630a and 630c (and haptics 630b and 630c, which are not shown in FIG. 6F), and haptics 640a and 640b. Haptics 640a and 640b may be integrally formed with membrane 610. In certain embodiments of the present invention, haptics 640a and 640b may be integrally formed with haptics 630a and 630b or integrally formed with 630b and 630d (not shown in FIG. 6F), or may be attached by various known mechanical attachment methods. Haptics 640a and 640b may resemble haptics 330a and 330b of device 300, described above. In certain embodiments of the present invention, device 690 may not comprise membrane 610, but rather may comprise ring 260 having opening 270 (ring 270 and opening 270 not shown in FIG. 6F).

Referring now to FIG. 6G, the placement of device 650 in cavity 25 is illustrated in a cross-sectional view. Haptics 630a and 630c are shown disposed along an exterior surface of anterior capsule 19, while haptics 630a and 630b are shown disposed along an interior surface of anterior capsule 19. Haptics 630a-630d in this configuration may, inter alia, enhance stability of device 650 in anterior capsule 19.

Figure 6H:
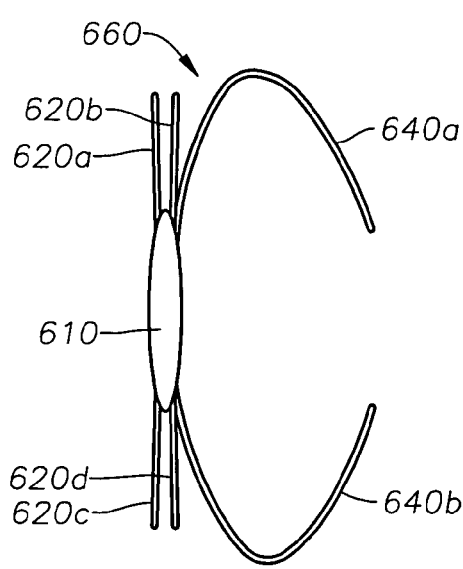
FIG. 6H shows a cross-sectional view of the device of FIG. 6E.

Referring now to FIG. 6H, device 660 is shown in side view. Device 660 previously has been described above, with reference to FIG. 6E.

Figure 6I:
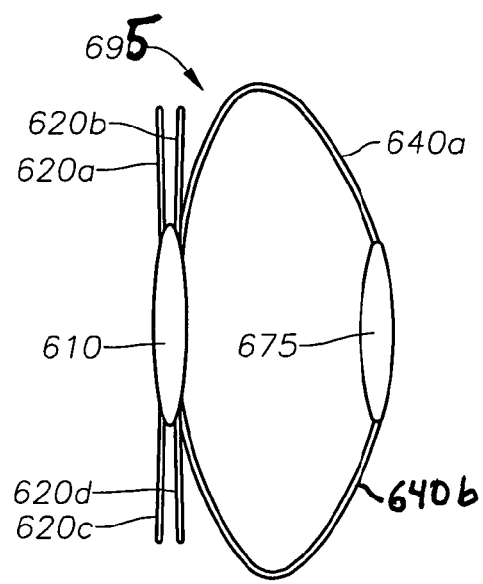
FIG. 6I shows a cross-sectional view of an embodiment of a device of the present invention.

Referring now to FIG. 6I, illustrated therein is a side view of another embodiment of a device of the present invention. Device 695 comprises membrane 610, haptics 620a-620d, haptics 640a and 640b, and optic 675. Optic 675 may be any suitable optic, for example, any of the optics described herein. In certain embodiments of the present invention, haptics 640a and 640b may be integrally formed with membrane 610. In certain embodiments of the present invention, haptics 640a and 640b may be integrally formed with haptics 620b and 620d, or may be attached by various known mechanical attachment methods. Haptics 640a and 640b may be formed as previously described herein (e.g., for haptics 330a and 330b, of device 300, described above). Haptics 640a and 640b of device 695 are shown attached to optic 675. In certain embodiments of the present invention, device 695 may not comprise membrane 610, but rather may comprise ring 260 having opening 270 (ring 270 and opening 270 not shown in FIG. 6I).

Figure 6K:
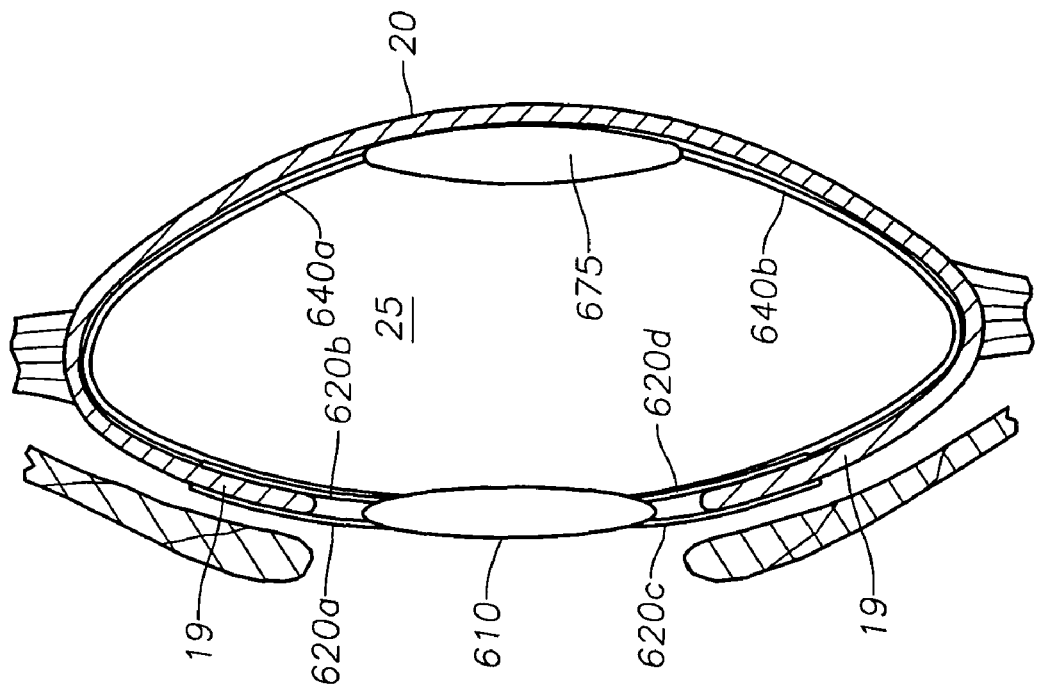
FIG. 6K shows a cross-sectional view of the anterior portion of a human eye in which the device of FIG. 6I has been placed.
Figure 6J:
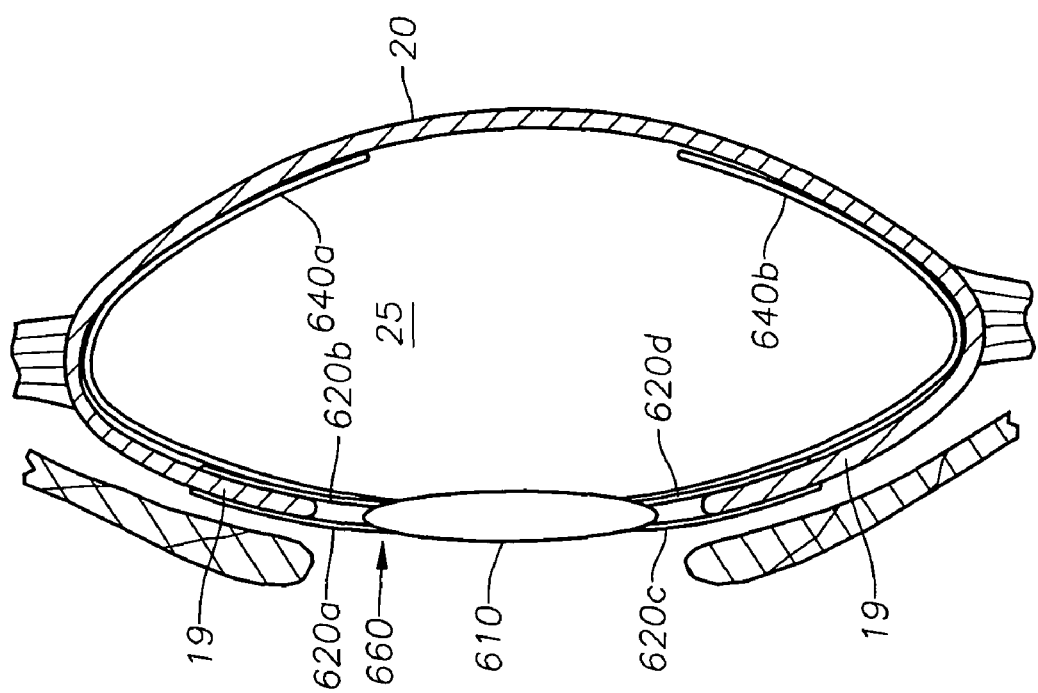
FIG. 6J shows a cross-sectional view of the anterior portion of a human eye in which the device of FIG. 6H has been placed.

Referring now to FIG. 6J, the placement of device 660 in cavity 25 is illustrated in a cross-sectional view. Haptics 620a and 620c are shown disposed along an exterior surface of anterior capsule 19, while haptics 620b, 620d, 640a, and 640b are illustrated disposed in the interior of anterior capsule 19 (with haptics 620b and 620d illustrated disposed along an interior surface of anterior capsule 19). Haptics 620a-620d, in this configuration, may, inter alia, enhance the stability of device 660 in anterior capsule 19. Haptics 640a and 640b may support for anterior capsule 19 and posterior capsule 20, in a manner that may enhance separation of anterior capsule 19 and posterior capsule 20, and that may enhance the volume of cavity 25 to a desired volume, which in certain embodiments may be a volume that may approach or equal that of a normal capsule volume (e.g., the volume of the capsule prior to its evacuation).

Referring now to FIG. 6K, the placement of device 695 in cavity 25 is illustrated in a cross-sectional view. Haptics 620*a* and 620*c* are illustrated disposed along an exterior surface of anterior capsule 19, while haptics 620*a*, 620*b*, 640*b*, and 640*d* are illustrated disposed in the interior of anterior capsule 19 (with haptics 620*b* and 620*d* illustrated disposed along an interior surface of anterior capsule 19). Haptics 620*a*-620*d*, in this configuration, may, inter alia, enhance the stability of device 695 in anterior capsule 19. Haptics 640*a* and 640*b* may support for anterior capsule 19 and posterior capsule 20, in a manner that may enhance separation of anterior capsule 19 and posterior capsule 20, and that may enhance the volume of cavity 25 to a desired volume, which in certain embodiments may be a volume that may approach or equal that of a normal capsule volume (e.g., the volume of the capsule prior to its evacuation).

In certain embodiments of the present invention, a second, "anterior" optic (not shown in FIG. 6K) may be integrally formed with membrane 610 or attached to ring 260 (not shown in FIG. 6K). In this application, device 695 may function as an accommodating IOL. Movement of the second, "anterior" optic (not shown) and posterior optic 675 in an anterior or posterior direction, caused by ciliary muscle 17 (shown in FIG. 1), may provide accommodation.

Referring now to FIG. 7A, a top plan view of another embodiment of a device of the present invention is illustrated therein. Device 700 comprises membrane 710, haptics 720, and haptics 730. Haptics 720 and haptics 730 may be integrally formed with membrane 710, or may be integrally formed to one another (not shown in FIG. 7A), or may be attached by various known mechanical attachment methods (not shown in FIG. 7A). Haptics 720 and haptics 730 may resemble haptics previously described herein (e.g., haptics 420*a* of device 400, described above). FIG. 7B shows a side view of an embodiment of device 700, in which haptics 720 and haptics 730 are shown integrally formed with, and extending from, membrane 710. In certain embodiments of the present invention, device 700 may not comprise membrane 710, but rather may comprise ring 260 having opening 270 (ring 260 and opening 270 not shown in FIG. 7B).

Referring now to FIG. 7C, the placement of device 700 in cavity 25 is illustrated in a cross-sectional view. Haptics 720 are illustrated disposed along an exterior surface of anterior capsule 19, while haptics 730 are illustrated disposed along an interior surface of anterior capsule 19. Haptics 720 and 730, in this configuration, may, inter alia, enhance stability of device 700 in anterior capsule 19.

Referring now to FIG. 8A, illustrated therein is a top plan view of another embodiment of a device of the present invention. Device 800 comprises membrane 810, and haptics 820*a*-820*d*. Haptics 820*a*-820*d* may be integrally formed with membrane 810, or may be attached by various known mechanical attachment methods. In certain embodiments of the present invention, device 800 may not comprise membrane 810, but rather may comprise ring 260 having opening 270 disposed within ring 260 (ring 260 and opening 270 not shown in FIG. 8A). In other embodiments of the present invention, an optic (not shown in FIG. 8A) may be integrally formed with membrane 810, or may be attached to ring 260 (not shown in FIG. 8A).

Figure 8B:
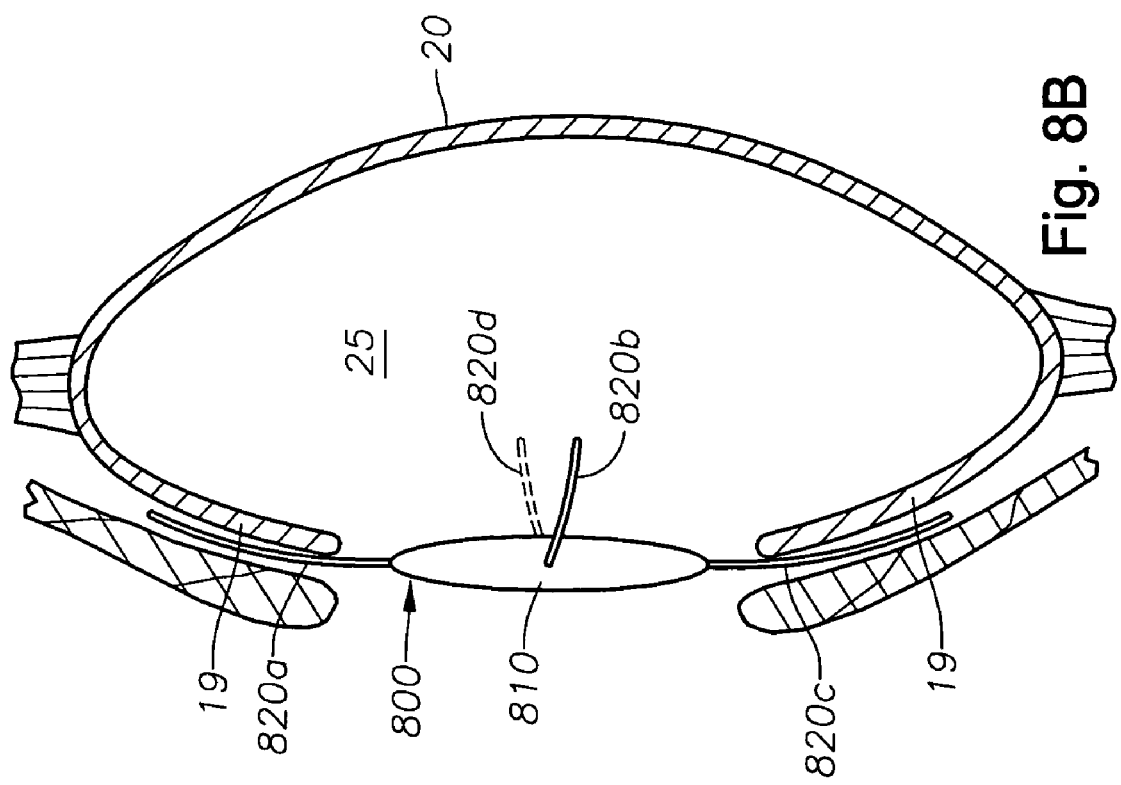
FIG. 8B shows a cross-sectional view of the anterior portion of a human eye in which the device of FIG. 8A has been placed.

Referring now to FIG. 8B, the placement of device 800 in cavity 25 is illustrated in a cross-sectional view. Haptics 820*a* and 820*c* are shown disposed along an exterior surface of anterior capsule 19. Haptics 820*b* and 820*d* may be adapted to be disposed along an exterior surface of anterior capsule 19 or along an interior surface of anterior capsule 19. Haptics 820*a*-820*d*, in this configuration, may, inter alia, enhance stability of device 800 in anterior capsule 19. Haptics 820*b* and 820*d* may further provide support for anterior capsule 19 and posterior capsule 20.

Figure 9:
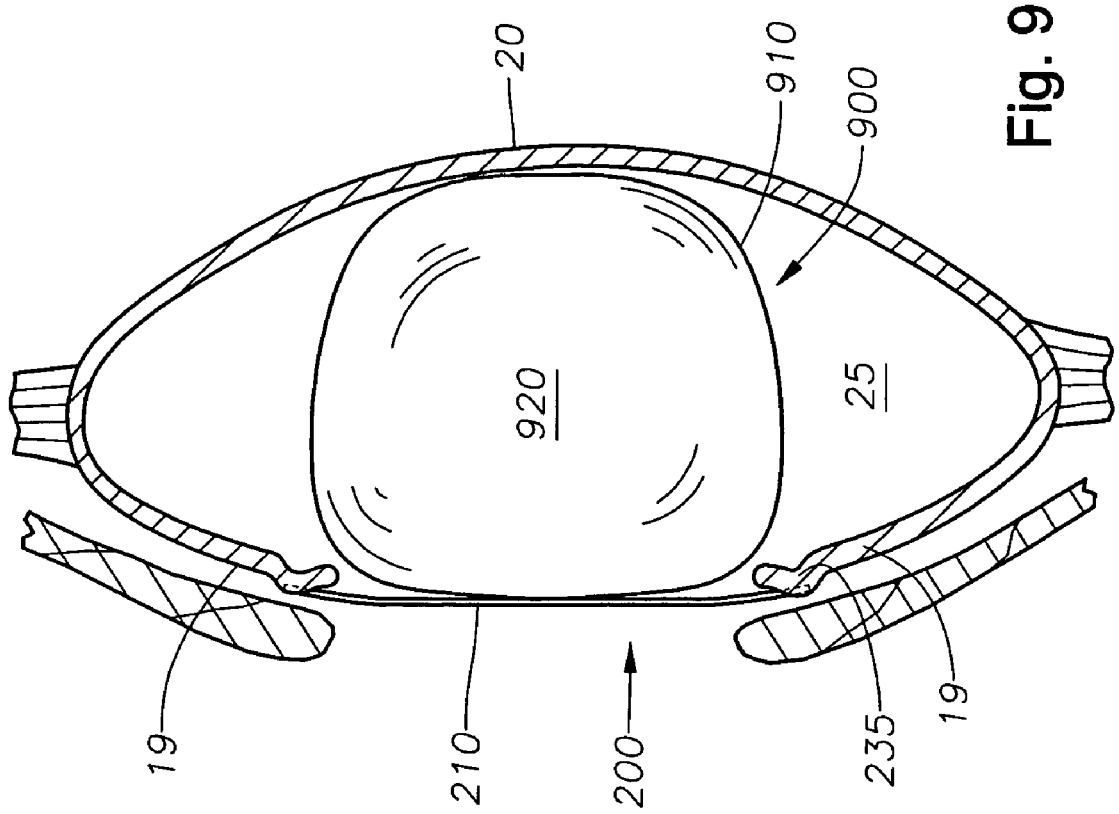
FIG. 9 shows a cross-sectional view of the anterior portion of a human eye in which both a bladder and the device of FIG. 2A have been placed.

Referring now to FIG. 9, an embodiment of a system of the present invention is illustrated therein in a cross-sectional side view. System 900 comprises device 200 and bladder 920. Bladder 920 comprises wall 910, which may circumscribe a sphere, or a sphere-like shape. Wall 910 may comprise any suitable deformable material. Normally, wall 910 will comprise a transparent material. Disposed within wall 910 of bladder 920 may be any suitable compound, such as, inter alia, air, a fluid, or a gel. In this application, device 200 may function as an artificial anterior capsule, while bladder 920 may provide shape and/or volume to cavity 25. In certain embodiments of the present invention, in which device 200 further comprises an optic (not shown in FIG. 9), system 900 may enhance accommodation. In such embodiments, movement of the optic (not shown) of device 200 in an anterior or posterior direction, caused by ciliary muscle 17 (shown in FIG. 1), may provide accommodation with the system 900 comprising device 200 and bladder 920. In certain other embodiments of the present invention, a system 900 optionally further comprise a posterior optic not shown in (FIG. 9) as described in commonly-owned U.S. patent application Ser. No. 10/027,743, the relevant disclosure of which is incorporated herein by reference.

The present invention also provides intraocular systems, which may comprise a plurality of devices of the present invention, or which may comprise a device of the present invention in combination with an ocular device known in the art. For example, some devices of the present invention may be combined with one or more of the devices disclosed in commonly-owned U.S. patent application Ser. No. 10/027,743.

In certain embodiments of the present invention, the devices of the present invention may be used to form an accommodating lens system. Such systems generally comprise an optic situated on the posterior capsule 20 (shown in FIG. 1). In some embodiments, the accommodating lens system may comprise an optic in both the posterior capsule 20 and anterior capsule 19 (shown in FIG. 1).

Other combinations of the devices disclosed herein may be used to obtain dual optic systems, adjusting haptics to allow placement of the devices in the capsular lens.

The devices of the present invention may be placed in the lens of an eye by a surgeon. Methods for such placement are known in the art, and include, inter alia, injection. Furthermore, the devices and systems of the present invention may be formed before placement, or may be formed, inter alia, by joining separate component parts after they are introduced into the eye or capsule. When the components are formed after placement, the components may be joined using any suitable method known in the art. For example, the devices may be welded or mechanically attached. Welds and methods of welding are known in the art and include, inter alia, tissue adhesives, heat welds, and laser welds. Examples of mechanical attachment can be found in commonly-owned U.S. patent application Ser. No. 10/027,743.

Although the disclosures herein have been primarily described with respect to application in human eyes, it should be understood that the apparatus and methods may be used in all animals, and reference to "eye" or "human eye" herein includes, inter alia, an eye of any animal.

Therefore, the present invention is well adapted to carry out the objects and attain the ends and advantages mentioned as well as those that are inherent therein. While the invention has been depicted and described with reference to embodiments of the invention, such a reference does not imply a limitation on the invention, and no such limitation is to be inferred. The invention is capable of considerable modification, alternation, and equivalents in form and function, as will occur to those ordinarily skilled in the pertinent arts and having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalents in all respects.

What I claim is:

1. A device for attachment to a capsule in an eye, the device comprising:
    a device body having a ring structure centrally disposed within the device body, the ring structure defining an opening centrally disposed therein; and
    at least one pair of outwardly extending elongated arms wherein a first arm cooperates with a second arm to form a pincer disposed along the device body, the first and second arms tapering to a pointed tip and adapted to pinch tissue therebetween for releasably attaching the device to a portion of the capsule.

2. The device of claim 1, wherein the device is formed from biocompatible material.

3. The device of claim 1, wherein the device has a selected response to a bending force so as to separate opposing regions of a capsulorhexis when at least a first pincer is releasably attached to a first region of the capsulorhexis and at least a second pincer is releasably attached to a second region of the capsulorhexis that is about opposite to the first region.

* * * * *